United States Patent
Hofmann et al.

(10) Patent No.: US 11,684,262 B2
(45) Date of Patent: Jun. 27, 2023

(54) PROVIDING A MEDICAL IMAGE

(71) Applicant: Siemens Healthcare GmbH, Erlangen (DE)

(72) Inventors: Christian Hofmann, Erlangen (DE); Andre Ritter, Neunkirchen am Brand (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 738 days.

(21) Appl. No.: 16/253,270

(22) Filed: Jan. 22, 2019

(65) Prior Publication Data
US 2019/0231191 A1  Aug. 1, 2019

(30) Foreign Application Priority Data
Jan. 29, 2018  (EP) .................................... 18153903

(51) Int. Cl.
*A61B 5/00* (2006.01)
*G16H 30/40* (2018.01)
(Continued)

(52) U.S. Cl.
CPC ............ *A61B 5/0035* (2013.01); *A61B 5/055* (2013.01); *A61B 5/1128* (2013.01); *A61B 6/032* (2013.01);
(Continued)

(58) Field of Classification Search
CPC ..... A61B 5/0035; A61B 5/055; A61B 5/1128; A61B 5/0037; A61B 6/032; A61B 6/541;
(Continued)

(56) References Cited

U.S. PATENT DOCUMENTS 6,628,743 B1 * 9/2003 Drummond ............ G16H 30/20
378/15
6,847,933 B1 1/2005 Hastings
(Continued)

FOREIGN PATENT DOCUMENTS

CN         101628154 A    1/2010
CN         102855618 A    1/2013
(Continued)

OTHER PUBLICATIONS

German to English machine translation of Guckenberger et al. (EP34122028A1) (Year: 2018).*
(Continued)

*Primary Examiner* — Chao Sheng
(74) *Attorney, Agent, or Firm* — Harness, Dickey & Pierce, P.L.C.

(57) ABSTRACT

A method is for providing a medical image of a patient. The method includes acquiring medical measurement data of the patient, including a set of multiple sampled state combinations; a first state space, including first physiological states, and a second state space, including second physiological states, together spanning a third state space. Each of the combinations includes a state from the first and second state spaces, and the third state space includes the set of combinations. The method further includes generating a medical image of the patient using the medical measurement data acquired, including a further state combination; the further state combination including a state from the first and second state space, the third state space including the further state combination, and the further state combination lying within the third state space outside the set of combinations. Finally, the method includes providing the medical image of the patient generated.

17 Claims, 3 Drawing Sheets

(51) Int. Cl.
    *A61B 5/055*     (2006.01)
    *A61B 5/11*     (2006.01)
    *A61B 6/03*     (2006.01)
    *G01R 33/56*     (2006.01)
    *G06T 7/00*     (2017.01)
    *A61B 6/00*     (2006.01)
    *G01R 33/28*     (2006.01)

(52) U.S. Cl.
    CPC ........ *G01R 33/5601* (2013.01); *G06T 7/0012* (2013.01); *G16H 30/40* (2018.01); *A61B 5/0037* (2013.01); *A61B 6/541* (2013.01); *G01R 33/281* (2013.01); *G01R 33/5608* (2013.01)

(58) Field of Classification Search
    CPC ........ A61B 6/03; A61B 5/0205; G16H 30/40; G16H 30/00; G16H 30/20; G01R 33/5601; G01R 33/281; G01R 33/5608; G06T 7/0012
    See application file for complete search history.

(56) References Cited

U.S. PATENT DOCUMENTS

| | | |
|---|---|---|
| 2003/0011368 A1 | 1/2003 | Abe |
| 2006/0253261 A1 | 11/2006 | Maier et al. |
| 2007/0270689 A1* | 11/2007 | Lothert ................ A61B 6/5235 600/428 |
| 2008/0103386 A1* | 5/2008 | Kirsch ............... G01R 33/5601 600/420 |
| 2008/0226149 A1* | 9/2008 | Wischmann ......... A61B 6/5235 600/407 |
| 2009/0010513 A1 | 1/2009 | Kirsch |
| 2011/0305378 A1* | 12/2011 | Florent ................. A61B 6/507 382/130 |
| 2013/0004037 A1 | 1/2013 | Scheuering |
| 2013/0033262 A1 | 2/2013 | Porter |
| 2015/0087972 A1* | 3/2015 | Dumont ................ A61B 5/318 600/431 |
| 2015/0187073 A1 | 7/2015 | Stemmer |
| 2016/0030002 A1 | 2/2016 | Liao et al. |
| 2018/0233233 A1 | 8/2018 | Sharma et al. |

FOREIGN PATENT DOCUMENTS

| | | | |
|---|---|---|---|
| CN | 105433977 A | 3/2016 | |
| CN | 107256427 A | 10/2017 | |
| DE | 102016215105 A1 | 9/2017 | |
| EP | 3412208 | 12/2018 | |
| EP | 3412208 A1 * | 12/2018 | ............ G06T 7/337 |
| WO | WO 2017029314 A1 | 2/2017 | |

OTHER PUBLICATIONS

Extended European Search Report dated Aug. 1, 2019.
European Search Report for European Patent Application No. 18153903.2 dated May 30, 2018.
Office Action for European Patent Application No. 18153903.2 dated Dec. 10. 2018.

* cited by examiner

PROVIDING A MEDICAL IMAGE

PRIORITY STATEMENT

The present application hereby claims priority under 35 U.S.C. § 119 to European patent application number EP 18153903.2 filed Jan. 29, 2018, the entire contents of which are hereby incorporated herein by reference.

FIELD

Embodiments of the invention generally relate to a method for providing a medical image of a patient, a system for providing a medical image of a patient, and a computer program product.

BACKGROUND

In medical imaging, an imaging measurement sequence which can typically be performed in a medical imaging modality is preferably optimized in such a way that primarily a physiological state of a patient may be visible in a medical image. Owing to different technical challenges it is usually not possible, or possible only with a high investment of time and effort, to make multiple, in particular different, physiological states of the patient visible in the medical image, in particular when the medical image has a comparatively large measurement range or a plurality of medical images, which are each intended to include the physiological states, are distributed over the measurement range.

SUMMARY

The inventors have discovered that a problem may arise from the fact that first physiological states and second physiological states differ from one another in the respective dynamic. In particular owing to the different dynamics, the imaging measurement sequence may typically be optimized either with regard to the acquisition of the first physiological states or to the acquisition of the second physiological states.

Furthermore, the inventors have discovered that a maximum field of view of the medical imaging modality is generally smaller than the measurement range of the imaging measurement sequence that is necessary for the simultaneous acquisition of the first physiological states and the second physiological states. In other words, medical measurement data containing the first physiological states and the second physiological states may typically be acquired sequentially, in particular not simultaneously.

Embodiments of the invention disclose a method for providing a medical image of a patient, a system for providing a medical image of a patient, and a computer program product, wherein the medical image may include different physiological states or state combinations, preferably simultaneously.

Advantageous embodiments are described in the claims.

At least one embodiment is directed to a method for providing a medical image of a patient comprises the following steps:
  acquiring medical measurement data of the patient,
    wherein the medical measurement data comprises a set of multiple sampled state combinations,
    wherein a first state space contains first physiological states of the patient, wherein a second state space contains second physiological states of the patient, and wherein the first state space and the second state space together span a third state space,
    wherein each of the multiple sampled state combinations contains a state from the first state space and a state from the second state space,
    wherein the third state space comprises the set of multiple sampled state combinations,
  generating a medical image of the patient using the medical measurement data,
    wherein the medical image contains a further state combination,
    wherein the further state combination contains a state from the first state space and a state from the second state space,
    wherein the third state space contains the further state combination, and
    wherein the further state combination lies within the third state space outside of the set of multiple sampled state combinations, and
  providing the medical image of the patient.

An embodiment of the inventive system for providing a medical image of a patient comprises a computing unit. The computing unit is embodied in particular for implementing the control unit of the medical imaging modality, in particular when the control unit of the medical imaging modality is mapped in program code segments/modules. The computing unit can for example be connected via the network to the radiology information system and/or the PACS image archiving system for the purpose of acquiring the medical measurement data and/or providing the medical image. Alternatively or in addition, the system for providing the medical image of the patient may comprise the medical imaging modality and/or the monitor. In this case the computing unit is preferably connected to the medical imaging modality in such a way that the medical measurement data, in particular the raw data, can be transferred from the medical imaging modality to the computing unit.

An embodiment of the inventive computer program product comprises program code segments/modules which can be loaded into the computing unit in order to carry out at least one embodiment of the method for providing a medical image of a patient when the program code segments/modules are executed in the computing unit.

The computer program product may be a computer program or comprise a computer program. The computer program product comprises in particular the program code segments/modules, which map at least one embodiment of the inventive method steps. This enables at least one embodiment of the inventive method to be performed in a defined and reproducible manner, as well as allowing a check to be carried out in respect of a transfer of at least one embodiment of the inventive method. The computer program product is preferably configured in such a way that the computing unit can perform at least one embodiment of the inventive method steps by way of the computer program product. The program code segments/modules can in particular be loaded into a memory of the computing unit and typically be executed via a processor of the computing unit having access to the memory.

Typically, when the computer program product, in particular the program code segments/modules, is executed in the computing unit, all inventive embodiment variants of the described method can be performed. The computer program product is resident for example on a physical computer-readable medium and/or stored in digital form as a data packet in a computer network. The computer program product may represent the physical computer-readable medium and/or the data packet in the computer network.

In this way at least one embodiment of the invention may therefore also relate to the physical computer-readable medium and/or the data packet in the computer network. The physical computer-readable medium can usually be connected directly to the computing unit, for example by the physical computer-readable medium being inserted into a DVD drive or plugged into a USB port, thereby enabling the computing unit to access the physical computer-readable medium in particular in a read-only manner. The data packet can preferably be downloaded from the computer network. The computer network may contain the computing unit or be connected to the computing unit indirectly via a wide area network (WAN) or a (wireless) local area network (WLAN or LAN) connection. The computer program product may for example be stored digitally on a cloud server at a storage location of the computer network and transferred to the computing unit via the internet via the WAN and/or by via the WLAN or LAN, in particular by invoking a download link which points to the storage location of the computer program product.

BRIEF DESCRIPTION OF THE DRAWINGS

The invention is described and explained in more detail below with reference to the example embodiments illustrated in the figures. In the following description of the figures, structures and entities that remain substantially the same are labeled consistently with the same reference sign as on the first occurrence of the respective structure or entity.

In the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment is directed to a method for providing a medical image of a patient comprises the following steps:
  acquiring medical measurement data of the patient,
    wherein the medical measurement data comprises a set of multiple sampled state combinations,
    wherein a first state space contains first physiological states of the patient, wherein a second state space contains second physiological states of the patient, and wherein the first state space and the second state space together span a third state space,
    wherein each of the multiple sampled state combinations contains a state from the first state space and a state from the second state space,
    wherein the third state space comprises the set of multiple sampled state combinations,
  generating a medical image of the patient using the medical measurement data,
    wherein the medical image contains a further state combination, wherein the further state combination contains a state from the first state space and a state from the second state space, wherein the third state space contains the further state combination, and wherein the further state combination lies within the third state space outside of the set of multiple sampled state combinations, and providing the medical image of the patient.

The acquisition of the medical measurement data may comprise performing an imaging measurement sequence in a medical imaging modality. Typically, the patient is supported for example on a patient couch during the imaging measurement sequence in the medical imaging modality or positioned in the medical imaging modality. The medical imaging modality may comprise a computed tomography (CT) system, a magnetic resonance tomography (MRT) system, a conventional X-ray system, a positron emission tomography system, an ultrasound system or also other imaging modalities. The medical measurement data may preferably be acquired via the computed tomography system.

The medical measurement data may include for example raw data, in particular projection data of the computed tomography system, k-space data of the magnetic resonance tomography system, digital and/or analog radiographic images acquired by the conventional X-ray system, and/or multiple image data templates. The raw data and the multiple image data templates are usually different from one another in terms of a storage volume and an image format. Typically, the storage volume of the raw data is greater than the storage volume of the multiple image data templates. The medical measurement data, in particular the multiple image data templates, may be available for example in a DICOM image format (DICOM=Digital Imaging and Communications in Medicine). The multiple image data templates may be reconstructed for example using the raw data, in particular the projection data of the computed tomography system, the k-space data of the magnetic resonance tomography system and/or the digital and/or analog radiographic images acquired by the conventional X-ray system. The multiple image data templates may typically be present in the DICOM image format.

The multiple image data templates may preferably be calculated from the projection data of the computed tomography system, the multiple image data templates in this case comprising at least one computed tomography image. Generally, the at least one computed tomography image has a distribution of image values, in particular a Hounsfield Unit (HU) distribution. The method for providing the medical image, in particular a medical computed tomography image, of the patient may be performed in particular via the computed tomography system.

The medical measurement data may be transferred to and/or stored in a radiology information system (RIS) and/or a PACS image archiving system (PACS=Picture Archiving and Communication System). For example, the raw data and/or the multiple image data templates may be transferred to and/or stored in the radiology information system or the PACS image archiving system. In principle it is conceivable that the acquisition of the medical measurement data comprises a downloading of the medical measurement data from the radiology information system or the PACS image archiving system, for example.

A state from the first state space and a state from the second state space typically form a state combination from the set of multiple sampled state combinations. If each of the multiple sampled state combinations contains a state from the first state space and a state from the second state space, each of the multiple sampled state combinations has in particular two states. Typically, the number of dimensions of the third state space corresponds to a number of states of each state combination from the set of multiple sampled state combinations. If, for example, the third state space has more than two dimensions, then typically each of the multiple sampled state combinations likewise has more than two dimensions.

The first physiological states and the second physiological states may be sorted or merged according to intensity, time of occurrence, medical relevance, etc., preferably in ascending or descending order. The first physiological states and/or the second physiological states may for example occur regularly, in particular cyclically. The first physiological states and/or the second physiological states in each case form in particular a set, in particular a one-dimensional set, or a list, in particular a one-dimensional list, as a result of which the first state space or the second state space is specified, in particular spanned. In principle it is conceivable that the first physiological states and/or the second physiological states in each case form a multidimensional set or a multidimensional list, as a result of which, correspondingly, a multidimensional first state space or a multidimensional second state space may be specified in each case. Generally, the first physiological states differ from the second physiological states in such a way that the third state space may be spanned. In other words, the first state space lies at least partially outside the second state space, and vice versa. The first state space and the second state space form in particular two spatial axes of the third state space, an angle between the spatial axes preferably being greater than 0°, particularly advantageously equal to 90°. The spanning therefore means in particular that the first physiological states and the second physiological states differ at least in the respective category, as a result of which the third state space preferably has the angle between the spatial axes greater than 0°. Figuratively speaking, at the angle equal to 0°, the category of first physiological states is typically equal to the category of second physiological states. At the advantageous angle of 90°, there is typically no dependence between the first physiological states and the second physiological states, i.e. they each have a different category.

The first state space and the second state space in each case contain in particular such states as can be assigned to the respective category of states. If the first state space contains the first physiological states and the second state space contains the second physiological states, the first state space and the second state space typically have one dimension in each case. In other words, the first state space is in particular one-dimensional and the second state space is in particular one-dimensional. The first state space and/or the second state space and/or the third state space may be discrete or continuous. Typically, the first state space and/or the second state space are discrete prior to the acquisition and/or during the acquisition of the medical measurement data.

The dimensionality of the first state space, the second state space and/or the third state space is not limited to the statements made above. In particular a two-dimensional third state space is spanned by the one-dimensional first state space and the one-dimensional second state space. The third state space may have multiple dimensions, a number of dimensions being greater than 1. It is conceivable for example that the first state space has one dimension, the second state space two dimensions, and consequently the third state space three dimensions. Alternatively or in addition, it is conceivable that the first state space, the second state space and a further state space collectively span a third state space which in this case is typically at least three-dimensional. The foregoing and following statements concerning the two-dimensional third state space are representative of the example embodiments, the at least third state space having more than two dimensions.

The first state space and/or the second state space may for example be specified and/or determined prior to the acquisition, during the acquisition and/or after the acquisition of the medical measurement data. For example, prior to the acquisition of the medical measurement data, a user may set a measurement parameter of the imaging measurement sequence in such a way that the first state space preferably contains the first physiological states and/or the second state space preferably contains the second physiological states. The measurement parameter may for example contain designations of the first physiological states or of the second physiological states. In this case the medical measurement data acquired in accordance with the imaging measurement sequence typically comprises the first physiological states and/or the second physiological states.

In principle it is conceivable that prior to the acquisition of the medical measurement data, in particular prior to the downloading of the medical measurement data from the radiology information system and/or the PACS image archiving system, the user provides the first state space and/or the second state space via a state filter. The state filter may for example contain one or more states from the first state space and/or from the second state space.

The first state space and/or the second state space may for example be specified a first time by the user prior to the acquisition of the medical measurement data and a second time by the user after the acquisition of the medical measurement data. In this case the user may for example extend the first state space and/or the second state space by further respective states after the acquisition of the medical measurement data and/or replace certain states. For example, the user may in each case combine and/or weight and/or model states from the first state space and/or the second state space. The weighting may in particular comprise an averaging, a median calculation, an interpolation, an extrapolation, an addition and/or a subtraction. Since, typically, the third state space is dependent on the first state space and the second state space, the third state space is specified accordingly in particular during the specification of the first state space and/or the second state space.

Alternatively or in addition, the control unit of the medical imaging modality may for example automatically check and/or modify the state space specified by the user, in particular reduce or increase it in size.

Preferably, a control unit of the medical imaging modality is embodied to perform the imaging measurement sequence in such a way that the medical measurement data comprises the first physiological states and/or the second physiological states. Preferably, therefore, the medical measurement data is dependent on the first physiological states and/or the second physiological states. If the first state space is specified prior to the acquisition, the control unit of the medical imaging modality can preferably control the imaging measurement sequence prospectively, in particular selectively sample the third state space. In other words, the control unit of the medical imaging modality can determine which of the first physiological states and/or which of the second physiological states have already been acquired, and/or specify which of the first physiological states and/or which of the second physiological states can be acquired next. The control unit of the medical imaging modality can for example move the patient couch in such a way that the medical measurement data comprises the first physiological states and/or the second physiological states. The control unit of the medical imaging modality can in particular be moved in such a way that the imaging measurement sequence is controlled prospectively, in particular that the third state space is selectively sampled. The patient couch can be moved back and forth a number of times through a maximum field of view of the medical imaging modality during the acquisition of the medical measurement data.

The set of multiple sampled state combinations may for example be assigned to the medical measurement data prospectively or retrospectively. The prospective assignment comprises for example adding a state combination from the set of multiple sampled state combinations during the acquisition of the medical measurement data, in particular during the execution of the imaging measurement sequence in the medical imaging modality, to the medical measurement data. In this case the set of multiple sampled state combinations is determined via a physiological sensor system, for example.

The retrospective assignment may comprise for example determining the set of multiple sampled state combinations using the medical measurement data, the medical measurement data being analyzed for example via an image recognition algorithm and/or the set of multiple sampled state combinations being assigned to the medical measurement data in accordance with the image recognition algorithm.

In principle it is conceivable that one of the multiple sampled state combinations contains a state which is assigned to the medical measurement data prospectively, and a further state which is assigned to the medical measurement data retrospectively. It is furthermore conceivable that the medical measurement data comprises a state combination from the set of multiple sampled state combinations, one state of said state combination being assigned to the raw data, and a further state of said state combination being assigned to the multiple image data templates. The state combination from the set of multiple sampled state combinations may for example be stored as part of the DICOM image format, in particular in the header of the DICOM image format.

In principle it is also conceivable that after the acquisition of the medical measurement data, the set of multiple sampled state combinations, in particular the first physiological states and/or the second physiological states, is determined using the medical measurement data. In this case the first state space and the second state space are specified in accordance with the determined set of multiple sampled state combinations after the acquisition of the medical measurement data.

Alternatively or in addition, the control unit of the medical imaging modality or a control unit of the radiology information system may determine the first state space, in particular the first physiological states, and/or the second state space, in particular the second physiological states, during the acquisition of the medical measurement data, for example. In this case the control unit of the medical imaging modality for example is embodied in such a way as to determine the first physiological states and/or the second physiological states, and to determine or specify the first state space and/or the second state space.

The set of multiple sampled state combinations is contained in particular within the third state space. Typically, the set of multiple sampled state combinations may be described mathematically by the first state space and by the second state space, for example by way of a set function.

Usually, the medical measurement data can be subdivided into measurement data blocks, the set of multiple sampled state combinations being assigned to the respective measurement data blocks. One measurement data block may for example contain that medical measurement data which has been acquired during a time interval. Typically, the time interval can correlate with a temporal resolution of the imaging measurement sequence or correspond to the temporal resolution of the imaging measurement sequence. Alternatively or in addition, the measurement data block may contain that medical measurement data which comprises and/or maps a part, in particular a spatial segment, of a measurement range of the medical imaging modality. For example, the spatial segment may contain a z-position of the measurement range of the medical imaging modality and/or an extension of the measurement range along the z-axis of the medical imaging modality. The z-axis of the medical imaging modality is typically aligned in parallel with the patient couch. The measurement data blocks may each contain a state combination from the set of multiple sampled state combinations.

The medical image of the patient is reconstructed in particular using the medical measurement data. The medical image may be dependent on the first physiological states and/or the second physiological states. Typically, the medical image of the patient is stored in the DICOM image format. The medical image of the patient can preferably be transferred to the radiology information system and/or the PACS image archiving system. The generation of the medical image comprises in particular determining the medical image using the medical measurement data.

The further state combination can usually be assigned to the medical image during the generation of the medical image. The further state combination differs in particular from the set of multiple sampled state combinations in such a way that the medical measurement data contains only the set of multiple sampled state combinations. As a consequence, the further state combination is typically not part of the medical measurement data. The further state combination is in particular a non-sampled state combination. The further state combination may be called a virtual state combination and/or a model-based state combination.

Typically, the medical measurement data is acquired and/or sampled as a function of the set of multiple medical state combinations. The set of multiple medical state combinations can usually be assigned to the medical measurement data.

Typically, therefore, the further state combination differs from a sampled state combination in that the medical measurement data is acquired only for the set of multiple sampled state combinations, the set of multiple sampled state combinations not including the further state combination. The further state combination can in particular be specified or predefined, in particular by the user, independently of the medical measurement data and/or of the set of multiple sampled state combinations.

The further state combination is contained in particular within the third state space. Preferably, the further state combination may be described mathematically by the first state space and by the second state space, for example by way of a further set function.

The further state combination may contain a state from the first state space and/or a state from the second state space. Alternatively or in addition, the further state combination may contain a further state, which is assigned to the first state space and can extend the first state space, and/or a further state, which is assigned to the second state space and can expand the second state space. It is conceivable for example that the further state from the first state space has portions of multiple states from the first state space and/or portions of all states from the first state space. The further state from the first state space can be calculated for example in such a way that the further state corresponds to a mixed state according to the portions of the multiple states from the first state space and/or of all states from the first state space. In other words, the further state can be calculated by weighting, in particular by averaging, the portions of the multiple states from the first state space and/or of all states from the first state space. In principle, each state space, in particular the first state space, the second state space and/or the third state space, may contain the mixed state. In this case a normally discrete first state space and/or a normally discrete second state space may be transformed into a continuous first state space or into a continuous second state space by adding the mixed state, as a result of which usually the third state space likewise becomes continuous.

An intersection between the further state combination and the set of multiple sampled state combinations is typically equal to zero. The further state combination may typically be assigned to the medical image, but not to the medical measurement data. In other words, the further state combination is not contained in a list of the set of multiple sampled state combinations. Preferably, an overlap between the further state combination and the set of multiple sampled state combinations is impossible. Typically, the further state combination and the set of multiple sampled state combinations lie adjacent to one another within the third state space. Typically, a state of the further state combination is displaced relative to the set of multiple sampled state combinations along one dimension, in particular a spatial axis, of the third state space.

Providing the medical image may comprise transferring the medical image to the radiology information system and/or the PACS image archiving system. Alternatively or in addition, the medical image may be displayed, in particular to the user, on a monitor. The monitor is preferably embodied for example as connected for the purpose of downloading the medical image from the radiology information system or the PACS image archiving system and/or from the control unit of the medical imaging modality, and/or for the purpose of displaying the medical image. The user can specify or predefine the further state combination via the monitor and/or input device(s), for example. In principle it is conceivable that the medical image can be exchanged via a network which for example connects the radiology information system and/or the PACS image archiving system and/or the medical imaging modality, and for example be stored on or downloaded from a server. In addition to the medical image, the medical measurement data may for example be provided, in particular transferred to the radiology information system and/or the PACS image archiving system and/or displayed on the monitor.

Embodiments of the inventive method for providing the medical image of the patient affords in particular the following advantages:

The generation of the medical image for virtually any desired state combinations is advantageous in particular with regard to a reduction in the duration of the patient examination. Furthermore, the duration of the patient examination when the imaging measurement sequence is executed in the computed tomography system and/or in the conventional X-ray system typically correlates with an amount of X-ray radiation that is potentially harmful for the patient. As a result of the advantageous prospective control of the imaging measurement sequence, in particular the selective sampling of the third state space, it is possible to reduce the duration of the examination and preferably the X-ray dose corresponding to the X-ray radiation. It is particularly advantageous if in particular only the first state space and/or the second state space, taken individually, are fully mapped in the medical measurement data The set of multiple sampled state combinations is preferably only large enough for the first state space and the second state space to be mapped in the medical measurement data.

The method according to at least one embodiment of the invention in particular enables the medical image to be provided for a state combination of the third state space irrespective of whether the medical measurement data is acquired for said state combinations. This is advantageous in particular for the user when, after the acquisition of the medical measurement data, the user is able to generate and provide the medical image for a specific state combination for which no medical measurement data is acquired. A further advantage can be a replacement of the medical measurement data for the state combinations for which, for example, the acquisition of the medical measurement data is technically not possible or the same would have to be acquired once again due to an unsatisfactory data quality of the medical measurement data.

An embodiment variant provides that the medical image of the patient is generated in such a way using the medical measurement data that the further state combination and a state combination from the set of multiple sampled state combinations contain the same state from the first state space and/or the same state from the second state space. In other words, in this example embodiment, a state of the further state combination is displaced relative to the set of multiple sampled state combinations along only one dimension of the third state space. Preferably, the displaced state of the further state combination can easily be determined. In this embodiment variant, the further state combination is typically limited to those state combinations which are predefined by the first physiological states of the first state space and by the second physiological states of the second state space. In other words, the third state space can be discrete in this embodiment variant.

An embodiment variant provides that the medical measurement data continues to be acquired until the medical measurement data contains each state from the first state space and/or each state from the second state space once. This embodiment variant describes an example of the selective sampling of the third state space. For example, the control unit of the medical imaging modality may be embodied for determining the states from the first state space and/or the states from the second state space, the control unit preferably terminating the execution of the imaging measurement sequence as soon as the medical measurement data includes each state from the first state space and/or each state from the second state space once. In other words, the imaging measurement sequence is controlled in such a way that the medical measurement data contains each state from the first state space and/or each state from the second state space at least once.

Alternatively or in addition, during the acquisition of the medical measurement data where the medical measurement data is retrieved from the radiology information system or from the PACS image archiving system, the user can terminate the downloading of the medical measurement data as soon as the medical measurement data contains each state from the first state space and/or each state from the second state space once. This is advantageous in particular in this case when the user specifies the first state space and/or second state space in accordance with a medical issue prior to the acquisition and/or after the acquisition of the medical measurement data.

An embodiment variant provides that the medical measurement data continues to be acquired until the medical measurement data contains each state from the first state space and each state from the second state space only once. The control unit of the medical imaging modality is embodied for example in such a way that the medical measurement data is acquired only until the medical measurement data contains each state from the first state space and each state from the second state space only once. This example embodiment is particularly advantageous with regard to a minimum examination duration, in particular a minimum X-ray dose. This embodiment variant describes a particularly preferred example of the selective sampling of the third state space.

An embodiment variant provides that the first physiological states and the second physiological states are selected from the following list:
multiple respiratory states of the patient's breathing,
multiple contrast agent states of an accumulation of contrast agent in the patient,
multiple cardiovascular states of the patient's heart,
multiple morphological states of a tumor of the patient,
multiple functional states of an organ of the patient,
multiple joint states of an extremity of the patient.

The multiple respiratory states are typically cyclical and comprise for example the states inhalation, medium breathing and/or exhalation. The multiple contrast agent states comprise for example the states no contrast agent accumulation, increasing contrast agent accumulation, maximum contrast agent accumulation and/or decreasing contrast agent accumulation. The multiple contrast agent states are usually made possible by an injection of a contrast agent bolus into the patient. The cardiovascular states of the heart are typically cyclical and comprise in particular systolic and diastolic cardiac phases. The morphological states of the tumor comprise in particular neovascularization, tumor growth and necrosis. The functional states of the organ may comprise for example a fill state of the patient's bladder (from empty to full). The multiple joint states of the extremity of the patient comprise in particular an outstretched or bent arm.

In one example, the mixed state may comprise for example the multiple respiratory phases, the mixed state preferably being calculated and/or averaged according to the multiple respiratory phases.

The physiological sensor system may for example comprise a respiratory belt, an echocardiograph, a contrast agent pump and/or a camera. For example, the multiple respiratory states of the patient's breathing can be determined by way of the respiratory belt or the camera, it being possible to assign the multiple respiratory states to the medical measurement data. Alternatively or in addition, the multiple contrast agent states of the contrast agent accumulation in the patient may be acquired via the contrast agent pump and/or via the medical measurement data.

The first state space may contain first morphological states of the patient and/or first functional states of the patient. If the first state space contains the first morphological states of the patient and the first functional states of the patient, the first state space is in particular two-dimensional.

Alternatively or in addition, the multiple respiratory states, the multiple contrast agent states, the multiple cardiovascular states, the morphological states of the tumor, the functional states of the organ and/or the multiple joint states, for example, may in each case contain morphological substates and/or physiological substates and/or functional substates. For example, the multiple respiratory states of the patient's breathing may include first physiological respiratory states and second morphological respiratory states. In this case it is conceivable that the first state space contains physiological respiratory states and the second state space morphological respiratory states. This is advantageous in particular if, for example, the morphology and the physiology of the patient are changed due to the patient's breathing. In this case the patient's rib cage may rise during inhalation for example, as a result of which in particular the morphological respiratory state changes, and simultaneously in particular an air-to-water ratio varies in a lung of the patient, as a result of which the physiological respiratory state may be changed. Typically, the lifting of the rib cage would be evident in the medical measurement data as a displacement of the rib cage, while the variation in the air-to-water ratio may become apparent as a result of a change in, for example, an attenuation coefficient, in particular a Hounsfield unit, and/or a relaxation time (T1 time, T2 time, T2* time) and/or a proton density.

An embodiment variant provides that the first state space contains the multiple respiratory states of the patient's breathing and the second state space contains the multiple contrast agent states of the contrast agent accumulation in the patient. In this case the third state space contains a spatial axis across the multiple respiratory states and a spatial axis across the multiple contrast agent states. In principle it is conceivable that, for example, the further state space contains the cardiovascular states of the patient. It is particularly advantageous that the user can be provided with the medical image for any desired further state combination of the patient's breathing and the contrast agent accumulation.

An embodiment variant provides that the set of multiple sampled state combinations fills the third state space by up to and including 50 percent at a maximum. If, in one example, the first state space has two first physiological states and the second state space has two second physiological states, the medical measurement data preferably continues to be acquired until the set of multiple sampled state combinations preferably comprises two state combinations, the medical measurement data containing each state from the first state space and each state from the second state space only once. In this example, the further state combination and the set of multiple sampled state combinations fill the third state space preferably by up to 75 percent. Typically, the further state combination increases the filling of the third state space in combination with the set of multiple sampled state combinations. If the first state space and/or the second state space each have more than two states, the set of multiple sampled state combinations typically fills the third state space by less than 50 percent. The set of multiple sampled state combinations fills the third state space in particular by less than 30 percent, preferably by less than 20 percent or particularly advantageously by less than 10 percent.

An embodiment variant provides that the multiple image data templates are reconstructed using the medical measurement data, the medical image being generated using the multiple image data templates. Generally, the multiple image data templates are reconstructed initially using the raw data of the medical measurement data and the medical image is generated in a further step. This is advantageous in particular because the storage volume of the multiple image data templates is typically smaller than the storage volume of the raw data.

An embodiment variant provides that multiple medical images of the patient are generated using the medical measurement data, the multiple medical images containing a set of multiple further state combinations, each of the multiple further state combinations containing a state from the first state space and a state from the second state space, the third state space containing the set of multiple further state combinations, and the set of multiple further state combinations lying within the third state space outside the set of multiple sampled state combinations. An intersection between the set of multiple further state combinations and the set of multiple sampled state combinations is preferably equal to zero.

In particular the set of multiple sampled state combinations together with the further state combination, in particular together with the set of multiple further state combinations, fill the third state space by up to and including 90%, particularly advantageously by up to 100%. If the filling of the third state space amounts to 100%, either the medical image, in particular the multiple medical images, or the medical measurement data, in particular the multiple image data templates, is preferably available for each state combination of the first physiological states and the second physiological states.

An embodiment variant provides that the generation of the medical image comprises the following steps:
  determining a deformation field using the medical measurement data, wherein the further state combination is used as an input parameter during the determination, wherein the deformation field is determined in pairs in each case for the set of multiple sampled state combinations and/or for an interpolated state combination from the set of multiple sampled state combinations, and
  applying the deformation field to the medical measurement data.

The deformation field may comprise in particular a vector field which maps a change between a start state combination and a target state combination. The deformation field may comprise multiple vector fields which describe a path from the start state combination to the target state combination. Furthermore, the deformation field may correspond to an interpolation or an extrapolation of the medical measurement data. As a result of applying the deformation field, the medical measurement data is deformed, typically along the path, in such a way that the generated medical image contains the further state combination, in particular the target state combination. Preferably, the deformation can be reversed by inversion of the deformation field.

If the deformation field is determined in pairs in each case for the set of multiple sampled state combinations, the deformation field can contain the vector field for any desired pair from the set of multiple sampled state combinations. In other words, each state combination from the set of multiple sampled state combinations is in particular start state combination and target state combination for one vector field in each case. In addition, the deformation field has a further vector field, the further state combination corresponding to the target state combination and a state combination from the set of multiple sampled state combinations corresponding to the start state combination. The further vector field describes in particular a step in the deformation of the medical measurement data to the medical image. In this case the generation of the medical image comprises in particular a concatenation of the vector fields within the set of multiple sampled state combinations and the further vector field. The generation of the medical image comprises in particular at least the application of the further vector field to the medical measurement data.

If the deformation field for the interpolated state combination is determined from the set of multiple sampled state combinations, the further vector field describes a deformation between the interpolated state combination as start state combination and the further state combination as target state combination. In this case the interpolated state combination is the target state combination for each state combination from the set of multiple sampled state combinations. The interpolated state combination preferably lies within the third state space outside the set of multiple sampled state combinations, particularly advantageously between the first physiological states and the second physiological states. The interpolated state combination enables in particular a continuous sampling of the third state space. In other words, the interpolated state space requires the third state space to be continuous. In a particularly preferred embodiment, the interpolated state combination corresponds to an averaged state combination. If the first state space comprises the two states inhalation and exhalation and the second state space the two states no contrast agent accumulation and full contrast agent accumulation, then the averaged state combination corresponds for example to the medium breathing of the patient and the increasing contrast agent accumulation in the patient. It is furthermore particularly advantageous that the medical image can be generated only by the application of two vector fields, one of which corresponds to the further vector field.

An embodiment variant provides that the determining of the deformation field comprises a modeling and/or a registering of the medical measurement data. The modeling and/or the registering of the medical measurement data may be performed separately, partially or generally for the first state space, the second state space and/or the third state space. The modeling and/or the registering of the medical measurement data may include using a physiological model, a structural model, an anatomical model and/or a morphological model. The modeling may require boundary conditions and/or fitting of mathematical functions. The modeling of the medical measurement data may include a cyclical boundary condition, as in the case of the multiple respiratory phases, for example. Alternatively or in addition, a model of the contrast agent accumulation, for example a gamma-variate function, can be fitted to the medical measurement data. The modeling of the medical measurement data enables in particular the continuous sampling of the third state space. The registering of the medical measurement data enables in particular a determination of the deformation field, in particular of the vector fields.

An embodiment variant provides that the generation of the medical image comprises the following further steps:
 subdividing the medical measurement data into a low-frequency measurement data portion and a high-frequency measurement data portion following the application of the deformation field, and
 combining the low-frequency measurement data portion and the deformed measurement data portion with different weightings, thereby generating the medical image.

Generally, the low-frequency measurement data portion and the high-frequency measurement data portion in combination produce the medical measurement data. Typically, the high-frequency measurement data portion includes information relating to edges and image noise, while the low-frequency measurement data portion includes information having low spatial frequency. In principle it is conceivable that the deformation field is applied separately to the high-frequency measurement data portion and to the low-frequency measurement data portion or that the deformation field is applied to the medical measurement data prior to its being subdivided. Preferably, the weighting in the combination of the low-frequency measurement data portion is different from the weighting in the combination of the high-frequency measurement data portion. For example, the high-frequency measurement data portion can be averaged and the low-frequency measurement data portion weighted by way of convex combination. It is furthermore conceivable that the weighting is specified locally, for example as a function or an organ of the patient, or globally. For example, the low-frequency measurement data portion of a lung of the patient may be weighted differently from the low-frequency measurement data portion of the patient's liver. Alternatively or in addition, the weighting may be dependent on an image intensity of the medical measurement data, in particular on the HU distribution.

An embodiment of the inventive system for providing a medical image of a patient comprises a computing unit. The computing unit is embodied in particular for implementing the control unit of the medical imaging modality, in particular when the control unit of the medical imaging modality is mapped in program code segments/modules. The computing unit can for example be connected via the network to the radiology information system and/or the PACS image archiving system for the purpose of acquiring the medical measurement data and/or providing the medical image. Alternatively or in addition, the system for providing the medical image of the patient may comprise the medical imaging modality and/or the monitor. In this case the computing unit is preferably connected to the medical imaging modality in such a way that the medical measurement data, in particular the raw data, can be transferred from the medical imaging modality to the computing unit.

An embodiment variant provides that the system comprises a computed tomography system which is embodied for acquiring the medical measurement data of the patient. In this example the system for providing the medical image of the patient comprises the medical imaging modality, in particular the computed tomography system. The computed tomography system comprises in particular an X-ray tube assembly and an X-ray detector, which are mounted so as to be rotatable around the patient couch. The control unit of the medical imaging modality is preferably embodied to control the computed tomography system, in particular the patient couch.

An embodiment of the inventive computer program product comprises program code segments/modules which can be loaded into the computing unit in order to carry out at least one embodiment of the method for providing a medical image of a patient when the program code segments/modules are executed in the computing unit.

The computer program product may be a computer program or comprise a computer program. The computer program product comprises in particular the program code segments/modules, which map at least one embodiment of the inventive method steps. This enables at least one embodiment of the inventive method to be performed in a defined and reproducible manner, as well as allowing a check to be carried out in respect of a transfer of at least one embodiment of the inventive method. The computer program product is preferably configured in such a way that the computing unit can perform at least one embodiment of the inventive method steps by way of the computer program product. The program code segments/modules can in particular be loaded into a memory of the computing unit and typically be executed via a processor of the computing unit having access to the memory.

Typically, when the computer program product, in particular the program code segments/modules, is executed in the computing unit, all inventive embodiment variants of the described method can be performed. The computer program product is resident for example on a physical computer-readable medium and/or stored in digital form as a data packet in a computer network. The computer program product may represent the physical computer-readable medium and/or the data packet in the computer network.

In this way at least one embodiment of the invention may therefore also relate to the physical computer-readable medium and/or the data packet in the computer network. The physical computer-readable medium can usually be connected directly to the computing unit, for example by the physical computer-readable medium being inserted into a DVD drive or plugged into a USB port, thereby enabling the computing unit to access the physical computer-readable medium in particular in a read-only manner. The data packet can preferably be downloaded from the computer network. The computer network may contain the computing unit or be connected to the computing unit indirectly via a wide area network (WAN) or a (wireless) local area network (WLAN or LAN) connection. The computer program product may for example be stored digitally on a cloud server at a storage location of the computer network and transferred to the computing unit via the internet via the WAN and/or by via the WLAN or LAN, in particular by invoking a download link which points to the storage location of the computer program product.

Figure 1:
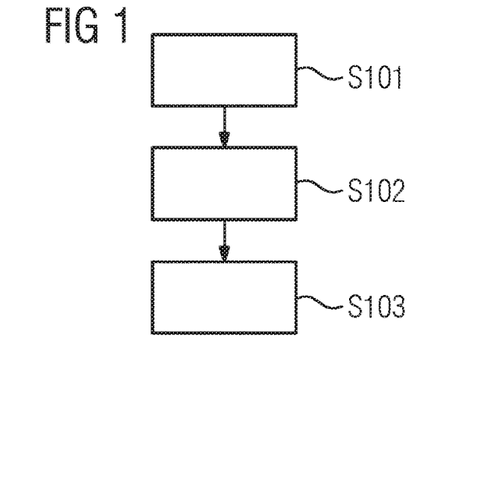
FIG. 1 shows a flowchart of a method for providing a medical image of a patient in a first example embodiment.

FIG. 1 shows a flowchart of a method for providing a medical image of a patient in a first example embodiment.

Method step S101 denotes the acquisition of medical measurement data of the patient, wherein the medical measurement data comprises a set of multiple sampled state combinations, wherein a first state space contains first physiological states of the patient, wherein a second state space contains second physiological states of the patient, and wherein the first state space and the second state space together span a third state space, wherein each of the multiple sampled state combinations contains a state from the first state space and a state from the second state space, and wherein the third state space comprises the set of multiple sampled state combinations.

Method step S102 denotes the generation of a medical image of the patient using the medical measurement data, wherein the medical image contains a further state combination, wherein the further state combination comprises a state from the first state space and a state from the second state space, wherein the third state space contains the further state combination, and wherein the further state combination lies within the third state space outside the set of multiple sampled state combinations.

Method step S103 denotes the providing of the medical image of the patient.

Figure 2:
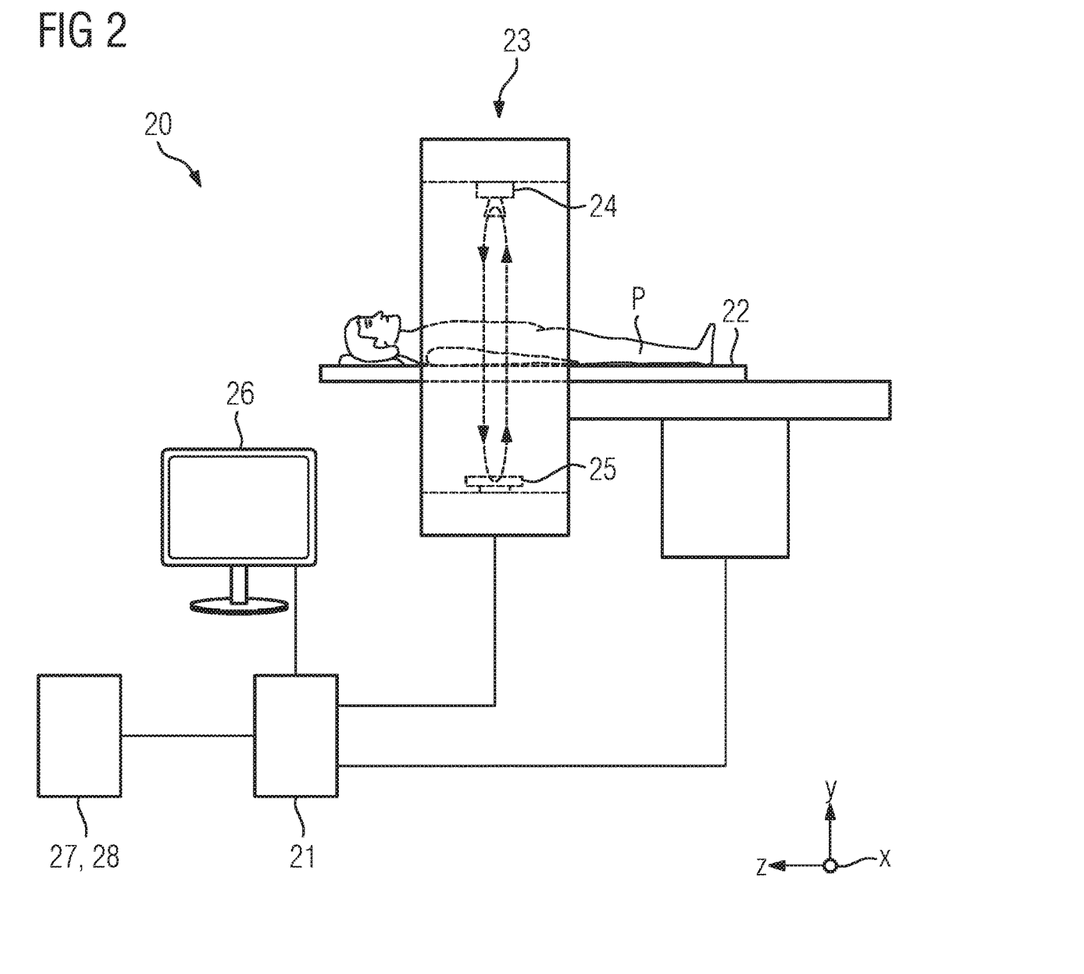
FIG. 2 shows a system for providing a medical image of a patient.

FIG. 2 shows the system 20 for providing the medical image of the patient P, the system 20 comprising a computing unit 21. The patient P is supported on a patient couch 22, the patient couch 22 being embodied in parallel with the z-axis. The computing unit 21 comprises a monitor 26 featuring for example a graphical user interface as well as input device(s). The computing unit 21 is connected to a radiology information system 27 and to a PACS image archiving system 28.

The system 20 comprises a computed tomography system 23 which is embodied for acquiring the medical measurement data of the patient P. The computed tomography system 23 comprises an X-ray tube assembly 24 and an X-ray detector 25, the X-ray tube assembly 24 and the X-ray detector 25 being arranged so as to be rotatable around the patient couch 22.

Figure 3:
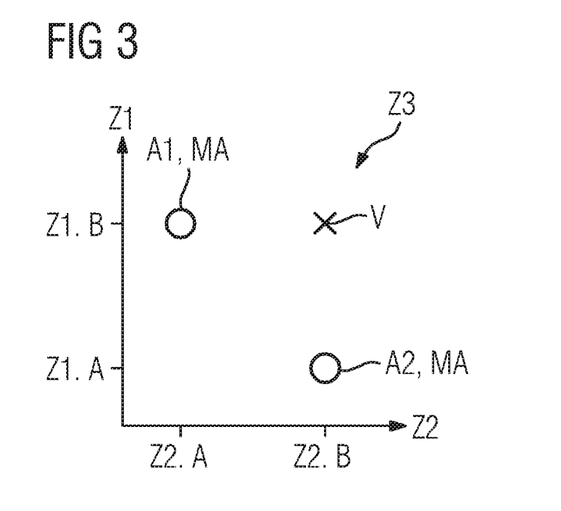
FIG. 3 shows a schematic representation of a third state space in a second example embodiment.

FIG. 3 shows a schematic representation of the third state space Z3 in a second example embodiment. The first state space Z1 contains the first physiological states Z1.A and Z1.B. The second state space Z2 contains the second physiological states Z2.A and Z2.B. The first state space Z1 and the second state space Z2 together span the third state space Z3, each of the multiple sampled state combinations A1, A2 including a state Z1.A, Z1.B from the first state space Z1 and a state Z2.A, Z2.B from the second state space Z2. The third state space Z3 contains the set MA of multiple sampled state combinations A1, A2. The further state combination V lies within the third state space Z3 outside the set MA of multiple sampled state combinations A1, A2.

The medical measurement data, for example raw data or the multiple image data templates, is available for the set MA of multiple sampled state combinations A1, A2. The medical image contains the further state combination V.

FIG. 3 indicates the result of the example embodiment when the medical measurement data continues to be acquired until the medical measurement data contains each state Z1.A, Z1.B from the first state space Z1 and each state Z2.A, Z2.B from the second state space Z2 once.

This schematic representation also corresponds to that example embodiment when the medical measurement data continues to be acquired until the medical measurement data contains each state Z1.A, Z1.B from the first state space Z1 and each state Z2.A, Z2.B from the second state space Z2 only once.

The set MA of multiple sampled state combinations A1, A2 fills the third state space Z3 by up to and including 50 percent at a maximum.

Figure 4:
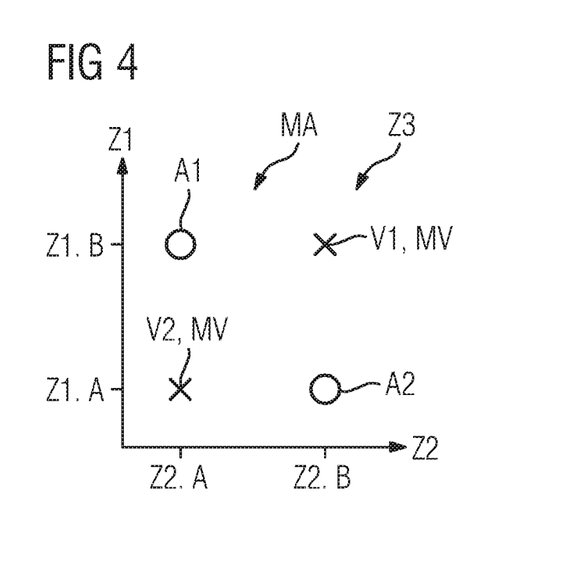
FIG. 4 shows a schematic representation of a third state space in a third example embodiment.

FIG. 4 shows a schematic representation of the third state space Z3 in a third example embodiment. Multiple medical images of the patient P are generated using the medical measurement data, wherein the multiple medical images comprise a set MV of multiple further state combinations V1, V2, wherein each of the multiple further state combinations V1, V2 contains a state Z1.A, Z1.B from the first state space Z1 and a state Z2.A, Z2.B from the second state space Z2, wherein the third state space Z3 contains the set MV of multiple further state combinations V1, V2, and wherein the set MV of multiple further state combinations V1, V2 lies within the third state space Z3 outside the set MA of multiple sampled state combinations A1, A2.

In principle it is conceivable that the multiple medical images of the set MV of multiple further state combinations are provided together with the medical measurement data, in particular the multiple image data templates, of the set MA of the multiple sampled state combinations.

Figure 5:
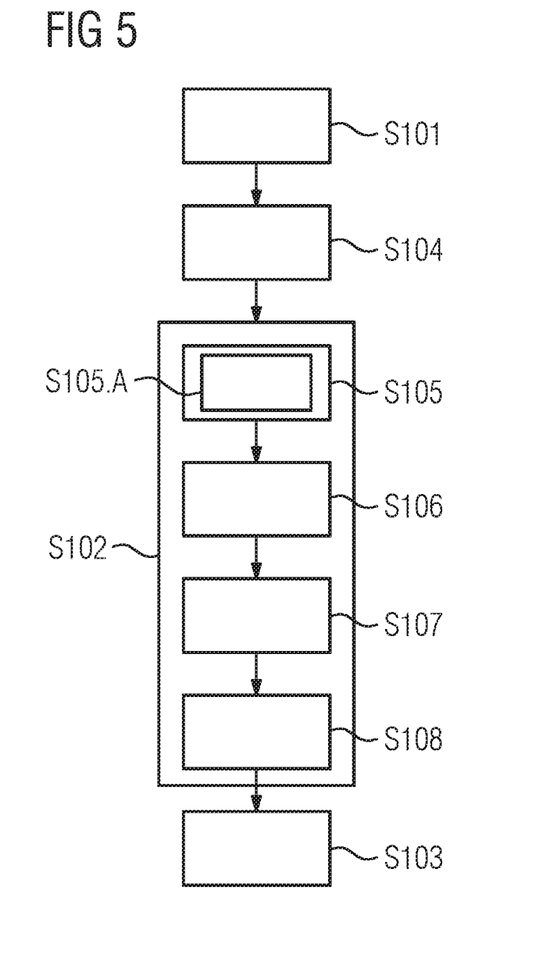
FIG. 5 shows a flowchart of the method in a fourth example embodiment.

FIG. 5 shows a first flowchart of a method for providing a medical image of a patient in a fourth example embodiment. The method steps S104 to S108 shown in FIG. 5 may be combined virtually as desired.

Method step S104 denotes that multiple image data templates are reconstructed using the medical measurement data, the medical image being generated using the multiple image data templates.

Method step S105 denotes the determining of a deformation field using the medical measurement data, in particular the multiple image data templates, wherein the further state combination is used as an input parameter during the determination, wherein the deformation field is determined in pairs in each case for the set of multiple sampled state combinations and/or for an interpolated state combination from the set of multiple sampled state combinations.

Method step S105.A denotes that the determining of the deformation field comprises a modeling and/or a registering of the medical measurement data, in particular of the multiple image data templates.

Method step S106 denotes the application of the deformation field to the medical measurement data, in particular to the multiple image data templates.

Method step S107 denotes the subdivision of the medical measurement data, in particular of the multiple image data templates, into a low-frequency measurement data portion and into a high-frequency measurement data portion following the application of the deformation field.

Method step S108 denotes the combining of the low-frequency measurement data portion and the high-frequency measurement data portion with different weightings, thereby generating the medical image.

Although the invention has been illustrated and described in greater detail on the basis of the preferred example embodiments, the invention is nonetheless not limited by the disclosed examples and other variations may be derived herefrom by the person skilled in the art without leaving the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing medical images of a patient, comprising:
   acquiring medical measurement data of the patient by a computed tomography (CT) system, the medical measurement data including a set of multiple sampled state combinations including a state from a first state space and a state from a second state space,
   wherein the first state space includes first physiological states of the patient,
   wherein the second state space includes second physiological states of the patient,
   wherein each of the first state space and second state space is at least one of multiple respiratory states of the patient's breathing, multiple contrast agent states of a contrast agent accumulation in the patient, multiple cardiovascular states of a heart of the patient, multiple morphological states of a tumor of the patient, multiple functional states of an organ of the patient, or multiple joint states of an extremity of the patient, and
   wherein the first state space and the second state space together span at least a portion of a third state space, the third state space being physiological state combinations not in the acquired medical measurement data;
   generating the medical images of the patient using the acquired medical measurement data, each of the medical images including a further state combination,
   wherein each of the further state combinations includes a state from the first state space and a state from the second state space,
   wherein the third state space includes the further state combinations,
   wherein the further state combinations lies within the third state space outside the set of multiple sampled state combinations, and the further state combinations are non-sampled state combinations, and
   wherein the generating of the medical images of the patient includes using the acquired medical measurement data in such a way that each of the further state combinations from the set of multiple sampled state combinations includes at least one of a same state from the first state space and a same state from the second state space, and at least one further state combination including the same state from the first state space, and another at least one further state combination including the same state from the second state space; and
   providing the medical images of the patient generated.

2. The method of claim 1, wherein the acquiring of the medical measurement data includes continuing to acquire the medical measurement data until the medical measurement data includes at least one of each state from the first state space and each state from the second state space once.

3. The method of claim 1, wherein the acquiring of the medical measurement data includes continuing to acquire the medical measurement data until the medical measurement data includes each state from the first state space and each state from the second state space only once.

4. The method of claim 1, wherein the first state space includes the multiple respiratory states of the breathing of the patient and wherein the second state space includes the multiple contrast agent states of the contrast agent accumulation in the patient.

5. The method of claim 1, wherein the set of multiple sampled state combinations fills the third state space by up to and including 50 percent.

6. The method of claim 1, the method further including reconstructing multiple image data templates using the medical measurement data and wherein the medical images are generated using the multiple image data templates.

7. A non-transitory machine-readable medium, on which program code segments of a computer program are stored, the program code segments being executable by a processor to carry out the method of claim 1 when the program code segments are executed by the processor.

8. The method of claim 1, wherein the acquiring of the medical measurement data includes continuing to acquire the medical measurement data until the medical measurement data includes at least one of each state from the first state space and each state from the second state space once.

9. The method of claim 1, wherein the acquiring of the medical measurement data includes continuing to acquire the medical measurement data until the medical measurement data includes each state from the first state space and each state from the second state space only once.

10. The method of claim 1, wherein the first state space includes the multiple respiratory states of the breathing of the patient and wherein the second state space includes the multiple contrast agent states of the contrast agent accumulation in the patient.

11. The method of claim 1, wherein the set of multiple sampled state combinations fills the third state space by up to and including 50 percent.

12. The method of claim 1, wherein the generating of the medical images comprises:
   determining a deformation field using the medical measurement data, wherein the further state combination is used as an input parameter during the determination, wherein the deformation field is determined in pairs for at least one of each of the set of multiple sampled state combinations and for an interpolated state combination from the set of multiple sampled state combinations, and
   applying the deformation field determined to the medical measurement data.

13. The method of claim 12, wherein the determining of the deformation field comprises at least one of a modeling of the medical measurement data and a registering of the medical measurement data.

14. The method of claim 12, wherein the generating of the medical images comprises:
   subdividing the medical measurement data into a low-frequency measurement data portion and a high-frequency measurement data portion following the applying of the deformation field, and
   combining the low-frequency measurement data portion and the high-frequency measurement data portion with different weightings, thereby generating the medical images.

15. The method of claim 14, wherein the different weighting includes the high-frequency measurement data portion being averaged and the low-frequency measurement data portion weighted by way of convex combination.

16. The method of claim 14, wherein the different weighting includes a first weighting for the low-frequency measurement data of a first organ or function, and a second weighting for the low-frequency measurement data of a second organ or function.

17. A system for providing medical images of a patient, comprising:
   a computing unit, wherein the computing unit is embodied for performing
   acquiring medical measurement data of the patient, the medical measurement data including a set of multiple sampled state combinations including a state from a first state space and a state from a second state space, the medical measurement data acquired by a computed tomography (CT) system,
      wherein a first state space includes first physiological states of the patient,
      wherein a second state space includes second physiological states of the patient,
      wherein the first state space and second state space are at least one of multiple respiratory states of the patient's breathing, multiple contrast agent states of a contrast agent accumulation in the patient, multiple cardiovascular states of a heart of the patient, multiple morphological states of a tumor of the patient, multiple functional states of an organ of the patient, or multiple joint states of an extremity of the patient, and
      wherein the first state space and the second state space together span at least a portion of a third state space, the third state space being physiological state combinations not in the acquired medical measurement data;
   generating the medical images of the patient using the acquired medical measurement data, each of the medical images including a further state combination,
      wherein each of the further state combinations includes a state from the first state space and a state from the second state space,
      wherein the third state space includes the further state combinations,
      wherein the further state combinations lies within the third state space outside the set of multiple sampled state combinations, and the further state combinations are non-sampled state combinations, and
      wherein the generating of the medical images of the patient includes using the acquired medical measurement data in such a way that each of the further state combination from the set of multiple sampled state combinations includes at least one of a same state from the first state space and a same state from the second state space, and at least one further state combination including the same state from the first state space, and another at least one further state combination including the same state from the second state space; and
   providing the medical images of the patient generated.

* * * * *